United States Patent [19]

Parenti

[11] Patent Number: 5,500,421
[45] Date of Patent: Mar. 19, 1996

[54] N-ALKYL-TAUROURODEOXYCHOLIC ACIDS AND THEIR THERAPEUTICALLY ACTIVE DERIVATIVES

[75] Inventor: Massimo Parenti, Novi Ligure (Alessandria), Italy

[73] Assignee: Prodotti Chimici Alimentari SPA, Basaluzzo, Italy

[21] Appl. No.: 196,790

[22] Filed: Feb. 15, 1994

Related U.S. Application Data

[63] Continuation of Ser. No. 870,372, Apr. 17, 1992, abandoned.

[30] Foreign Application Priority Data

Apr. 17, 1991 [IT] Italy .................... MI91A1059

[51] Int. Cl.$^6$ .................... A61K 31/575; C07J 9/00
[52] U.S. Cl. .................... 514/182; 552/554
[58] Field of Search .................... 552/554; 514/182

[56] References Cited

U.S. PATENT DOCUMENTS

| | | | |
|---|---|---|---|
| 3,580,936 | 5/1971 | Pattchett et al. | 552/554 |
| 3,622,669 | 11/1971 | Patchett et al. | 552/554 |
| 4,104,285 | 8/1978 | Gallo-Torres et al. | 552/554 |
| 4,565,810 | 1/1986 | Castagnola et al. | 552/554 |
| 4,892,868 | 1/1990 | Castagnola et al. | 514/182 |
| 5,122,520 | 6/1992 | Azria et al. | 552/554 |

FOREIGN PATENT DOCUMENTS 0400695 12/1990 European Pat. Off. .

OTHER PUBLICATIONS

Schmassmann et al "Prevention of Ursodeoxycholate . . . " Hepatology, vol. 11, No. 6, 1990, pp. 989–996.
Batta et al "Substrate Specificity of Cholylglycine . . . " Journal of Biological Chemistry, vol. 259, No. 24, 1984, pp. 15035–15039.

Primary Examiner—Kimberly J. Kestler
Attorney, Agent, or Firm—Nixon & Vanderhye

[57] ABSTRACT

The invention discloses N-alkyl-tauroursodeoxycholic acids and their pharmaceutically acceptable salts of the formula

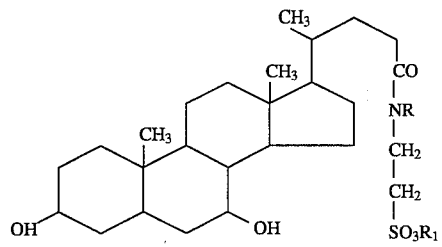

wherein R is a $C_2$–$C_4$ alkyl group and $R_1$ is hydrogen, an alkali metal, an alkaline earth metal or a radical of a basic amino acid.

The compounds are prepared by reacting a mixed anhydride of ursodeoxycholic acid and alkyltaurine followed by percolation through two columns respectively containing a strong cationic resin in $H^+$ form and a weakly anionic resin $OH^-$ form. The compounds are useful for the treatment of hepatic diseases.

3 Claims, No Drawings

N-ALKYL-TAUROURODEOXYCHOLIC ACIDS AND THEIR THERAPEUTICALLY ACTIVE DERIVATIVES

This is a continuation of application Ser. No. 07/870,372, filed Apr. 17, 1992, now abandoned.

The present invention relates to novel compounds, namely the N-alkyl-tauroursodeoxycholic acids and their pharmaceutically acceptable salts and derivatives, as well as to the process for their preparation and to their therapeutical use.

The therapeutical properties of the tauroursodeoxycholic acid are known, it being used in the treatment of diseases and troubles of the hepatic zone. Owing to the presence of the taurine as the conjugating aminoacid the compounds are physiological, since no metabolic conversion of the conjugate is necessary in order it to exploit its activity.

However recent studies carried out in the rabbit (A. Schmassmann et al, Hepatology 11, 989–96, 1990) and studies of enzimatic in vitro deconjugation (J. Lipid Res., 27, 742–52, 1986) have shown that the conjugate with taurine and glycine of the bile acids, particularly of the chenodeoxycholic and ursodeoxycholic acids are liable to a deconjugation by the colon bacteria and to a subsequent dehydroxylation leading to the product of their bacterial bioconversion, namely the lithocholic acid: this compound has a definite hepatotoxic action, which is shown through several not negligible side effects, almost proportionally to the amount of lithocholic acid which is formed.

The above mentioned studies have also revealed that the N-methyl derivatives of the ursodeoxycholic acid with glycine and taurine are resistant to the above described deconjugation whereby their administration to the experimental animal, particularly to the rabbit, does not lead in a quantitatively amount and in short time to the forming of lithocholic acid, with the attendant advantages in terms of hepatotoxicity. It has been now found and is the object of the present invention that the conjugates of ursodeoxycholic acid with N-alkyltaurine, wherein the alkyl group contains 1 to 4 carbon atoms, are endowed with interesting pharmacological properties besides the above cited one of being resistant to the deconjugation induced by the colon bacteria.

The compounds of the present invention have the following structural formula:

wherein R represents a $C_1$–$C_4$ alkyl, and $R_1$ represents H, an alkali or alkaline earth metal, or the radical of a basic aminoacid selected among lysine, arginine, ornithine and hystidine.

It is evident that among the compounds having the above formula, those in which R is a $C_2$–$C_4$ alkyl are novel, whereas for the N-methyl derivative the therapeutic use is herein claimed in the terms hereinafter explained.

In the present specification the compounds of the invention shall be hereinafter indicated as N-alkyl-TUDCA.

The N-alkyl-TUDCA molecules have important physiological and pharmaceutical properties, rendering them potentially useful in several pathologies of human beings.

The main properties on which the potential pharmacological activities are based are the following:
1) Effective absorption in the ileum, captation by the liver and bile secretion, without any lipid secretion.
2) Relevant choleretic-cholagogue activity, in terms both of biliary flow and of lipid secretion.
3) Characteristics of exceedingly high hydrophylicity, substantially like those of TUDCA.
4) Poor or absent intestinal deconjugation/dehydroxylation, due to the above cited bacterial enzymatic hydrolysis.

The first property permits the N-alkyl-TUDCA to be stored and concentrated in the enterohepatic circulation, which is the preliminary condition for their pharmacological actions.

The second property is the basis of the therapeutical potentiality of N-alkyl-TUDCA in the treatment of biliary calculi and dispepsia (since they promote a liquid-crystaline biliary secretion) and of dislipidemia (since they promote the removal of the cholesterol in the bile).

The third property (hydrophylicity) is the cause of the fact that N-akyl-TUDCA are not membrane-lesives but membrane protective. This fact is readily assessed from in vitro tests of haemolysis of normal human erythrocytes, in the presence of increasing amounts of the biliary salt.

Table 1 shows as N-alkyl-TUDCA, likewise TUDCA, are not haemolytic even at high concentrations (10 to 20 mM), differently from other physiological or synthetic biliary salts.

Other data indicate moreover that N-alkyl-TUDCA prevent the membrane damages induced from more hydrophobic biliary salts or from other toxic salts. Likewise it occurs with the other biliary salts, the data relating to erythrocytes can be extended to other cells (hepatocytes) and organs (liver).

The fourth property permits the N-alkyl-TUDCA not to be deconjugated and then conjugated again with glycine, thus preventing their possible dehydroxylation, leading to the forming a more hydrophobic compounds, like lithocholate.

Thus the therapeutical potentiality of the compounds of this invention in the treatment of acute and chronical hepatopathies is furthermore increased, and is at the basis of their therapeutical effect in the syndromes of bad absorption of different types.

TABLE 1

Percent erythrocytary haemolysis induced from several biliary acids at increasing concentrations.

| | Concentration of biliary salts | | | | | |
|---|---|---|---|---|---|---|
| | 0.6 mM | 1.25 mM | 2.5 mM | 5.0 mM | 10.0 mM | 20.0 mM |
| Glyco-UDCA | 0.7 | 1.3 | 1.3 | 7.9 | 8.8 | 17.1 |
| Sarco-UDCA | 1.0 | 1.6 | 2.3 | 5.7 | 29.8 | 96.5 |
| Tauro-UDCA | 1.2 | 1.1 | 1.5 | 1.7 | 2.3 | 3.3 |
| N-M-Tauro-UDCA | 0.7 | 0.4 | 1.3 | 2.7 | 2.1 | 8.0 |
| N-E-Tauro-UDCA | 0.5 | 0.6 | 1.1 | 2.4 | 2.1 | 7.2 |
| Tauro-DCA | 2.3 | 56.2 | 96.9 | 100 | 100 | 100 |

Incubation at 37° C. in isotonic saline solution
Legend:
Glyco-UDCA: glycoursodeoxycholic acid
Sarco-UDCA: sarcosyl-(N-methyl-glyco)-ursodeoxycholic acid
Tauro-UDCA: tauroursodeoxycholic acid
N-M-Tauro-UDCA: N-methyl-tauroursodeoxycholic acid
N-E-Tauro-UDCA: N-ethyl-tauroursodeoxycholic acid
Tauro-DCA: Taurodeoxycholic acid In view of the above mentioned properties the following therapeutical uses are foreseen for the compounds of the present invention:

1) Prevention and therapy of the biliary calculi.
2) Therapy of chronic and acute hepatopathies, including the following: cirrohosis of the liver, viral chronic hepatitis, alcoholic hepatopathy, self-immune hepatitis, primitive biliary cirrhosis, sclerosating cholangitis, cholestasis of several types.
3) Celiac disease, pancreatic insufficiency, cistic fibrosis.
4 Therapy of hyperlipoproteinaemia For the preparation of the N-alkyl-tauroursodeoxycholic acids of the present invention, having also the chemical name 2[[3α-5β-dihydroxy-24-oxo-5β-cholan-24-yl]alkylamino] ethansulphonic acids, the present invention comprises reacting the mixed anhydride of ursodeoxycholic acid, freshly prepared, with a solution of alkyltaurine in sodium hydrate, leading to the sodium salt of the desired N-alkyl-tauroursodeoxycholic acid, from which the desired acid is obtained by passing it through an ion exchange resin, whereby also the purification of the desired compound from undesired impurities, mainly chlorides, is simultaneously achieved, whereas the unreacted alkyltaurine and ursodeoxycholic acid are removed and recovered by standard methods well known in the specific prior art.

The present invention furthermore includes the pharmacologically acceptable derivatives of the N-alkyl-TUDCA of the invention, particularly the salts with alkali and earth-alkali metals and with basic aminoacids, particularly lysine, arginine, ornithyne and hystidine.

The preparation of the compounds according to the present invention is illustrated by the following example, obviously having merely illustrative and non limiting purpose, since there are possible and foreseable other methods, per se known in the art, for their preparation starting from the indicated reactants and particularly for the carrying out of the conjugation reaction.

EXAMPLE a) Mixed anhydride of ursodeoxycholic acid.

A solution of 40 g of ursodeoxycholic acid and 14.2 ml of triethylamine in 240 ml of dioxane, cooled at −10° C., is dropwise added with 9.7 ml of ethylchloroformiate. Since the reaction is exothermic, the temperature of the reaction mixture is maintained at the aforesaid value, by externally cooling with acetone and dry ice. Upon the addition of ethylchloroformiate is completed, the mixture is maintained under stirring, by leaving at the same time the temperature of the reaction mixture to increase up to room temperature.

The resulting suspension is filtered from the triethylamine hydrochloride and the remaining organic solution is used as such for the next step.

b) Sodium salt of N-methyltauroursodeoxycholic acid.

A solution is prepared comprising 17 g of N-methyltaurine in 122 m of 1N sodium hydroxide.

This solution is poured in the organic solution of mixed anhydride as previously prepared and the reaction mixture is maintained under stirring for 3 hours; then the filtration is effected for the removal of the unreacted methyltaurine.

c) N-methyltauroursodeoxycholic acid.

The solution of sodium salt of the methyltauroursodeoxycholic acid as above obtained (about 500 ml) is percolated through a column, filled with 100 ml of a strong cationic resin, Relite CF, in $H^+$ ion form, at a flow rate of 500 ml/h.

The solution of acid coming out of this column is percolated a second time through 100 ml of weak anionic resin, Relite GH1, in $OH^-$ ion form, again at a flow rate of 500 ml/h.

The percolated solution in concentrated to dryness under vacuum, maintaining the temperature to a value less than 50° C.

The dry residue is added with 120 ml of ethanol and the suspension is refluxed for one hour. The cooled suspension is filtered and from the resulting solution the desired product is precipitated by adding 3 liters of acetone cooled at 0° C.

After one night in a refrigerator, the acid is filtered and dried at 50° C. under vacuum.

The product is dissolved again in water, and precipitated on three liters of cool acetone giving 20 g of N-methyltauroursodeoxycholic acid having a 99% purity and melting point of 171°–173° C. with decomposition.

At the spectrographic analysis, the IR spectrum, effected on KBr, tablets, shows the peaks characteristic of the sulfonic acids, all expressed as $cm^{-1}$, at 1155 and 1045 and the O—H stretching band of the sulfonic group at 3440. The presence of the alcoholic groups is confirmed by the intense band at 1020 due to the C—OH streching which perhaps partially covers the band characteristic of the $SO_3H$ group at about 1045. The peaks of the secondary amido groups at 3300 and 3100, which are characteristic of the tauroursodeoxycholic acid, are absent.

At 1620 and 1580 the absorptions due to the carbonyl group are present.

These peaks, although hindered by the bands of the alcoholic and sulfonic OH, confirm the presence of the peptide bond between the ursodeoxycholic acid and the methyltaurine.

The other derivatives according to the present invention, namely the N-ethyl, N-propyl, N-isopropyl, N-butyl and N-isobutyl tauroursodeoxycholic acids are prepared in the same manner using the corresponding N-alkyl-taurine.

The resulting acids have no defined melting point and their IR spectrum can be practically overlapped to that of the N-methyl-tauroursodeoxycholic acid.

The pharmacologically acceptable salts and particularly those with alkali and earth-alkali metals as well as with basic aminoacids are prepared with the methods known from the prior art.

For the pharmaceutical compositions reference is made to the pharmaceutical compositions already known and described for the taurorsodeoxycholic acid, it holding true also as regards the dosages and posologies.

I claim:

1. A conjugated derivative of tauroursodeoxycholic acid of the formula

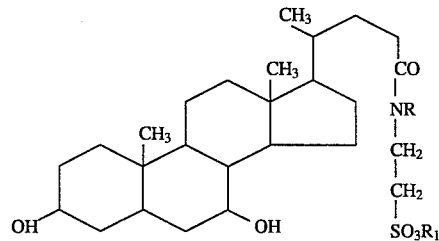

wherein R is $C_2$–$C_4$ alkyl and $R_1$ is hydrogen, an alkali metal, an alkaline earth metal or a radical of a basic amino acid.

2. A conjugated derivative according to claim 1, wherein said basic amino acid is selected from the group consisting of lysine, arginine, ornithine and histidine.

3. A pharmaceutical composition comprising as active ingredient a conjugated derivative according to claim 1 in association with an excipient or vehicle.

* * * * *